United States Patent [19]

Barth et al.

[11] Patent Number: 4,612,311

[45] Date of Patent: Sep. 16, 1986

[54] 1,2,4-BENZOTHIADIAZINE OXIDE DERIVATIVES

[75] Inventors: Hubert Barth, Emmendingen; Johannes Hartenstein, Stegen-Wittental; Gerhard Satzinger, Denzlingen; Edgar Fritschi, St. Peter; Hartmut Osswald; Gerd Bartoszyk, both of Waldkirch, all of Fed. Rep. of Germany

[73] Assignee: Warner-Lambert Company, Morris Plains, N.J.

[21] Appl. No.: 772,501

[22] Filed: Sep. 4, 1985

[30] Foreign Application Priority Data

Sep. 8, 1984 [DE] Fed. Rep. of Germany ....... 3433037

[51] Int. Cl.⁴ .................... C07D 513/04; A61K 31/54
[52] U.S. Cl. ........................................ 514/222; 544/9
[58] Field of Search ............................ 544/9; 514/222

[56] References Cited

U.S. PATENT DOCUMENTS

| 3,257,395 | 6/1966 | Griot | 544/9 |
| 3,294,791 | 12/1966 | Wei et al. | 544/9 |
| 3,311,620 | 3/1967 | Bell et al. | 544/9 |
| 3,471,483 | 10/1969 | Bell | 544/9 |
| 3,637,684 | 1/1972 | Goldman | 544/9 |
| 3,954,984 | 5/1976 | Albrecht | 544/9 |

FOREIGN PATENT DOCUMENTS 60-78990  5/1985  Japan ...................... 544/9

Primary Examiner—John M. Ford
Attorney, Agent, or Firm—Ronald A. Daignault

[57] ABSTRACT

1,2,4-Benzothiadiazine oxide derivatives of the general Formula I

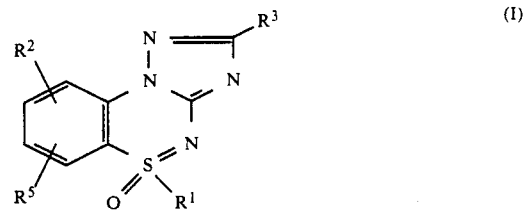

in which
$R^1$ represents an unsubstituted or substituted aryl radical;
$R^2$ and $R^5$, which may be the same or different, and represent hydrogen, halogen, or a nitro group, and
$R^3$ represents a hydrogen atom or a hydroxy radical, an alkyl, alkoxy alkyl or alkoxy carbonyl radical with up to four carbon atoms, unsubstituted or substituted by halogen, hydroxy, amino, alkyl amino or dialkyl amino radicals, or a phenyl radical, unsubstituted or substituted by halogen, are described as having anxiolytic effects on the central nervous system.

10 Claims, No Drawings

1,2,4-BENZOTHIADIAZINE OXIDE DERIVATIVES

SUMMARY OF THE INVENTION

The present invention relates to 1,2,4-benzothiadiazine oxide derivatives, to anxiolytic pharmaceutical compositions containing such derivatives and to a method of treating states of anxiety with an anxiolytic pharmaceutical composition containing such a derivative in unit dosage form.

The 1,2,4-benzothiadiazine oxide derivatives are those of the general Formula I:

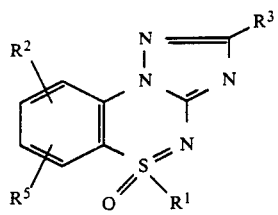

in which
R$^1$ represents an unsubstituted or substituted aryl radical;
R$^2$ and R$^5$ which may be the same or different, represent a hydrogen or halogen atom or a nitro group; and
R$^3$ represents a hydrogen or hydroxy radical, an alkyl, alkoxy alkyl or alkoxy carbonyl radical with up to four carbon atoms, unsubstituted or substituted by halogen, hydroxy, amino, alkyl amino or dialkyl amino radicals or a phenyl radical, unsubstituted or substituted by halogen; their optical isomers; or pharmaceutically acceptable acid addition salts thereof.

DETAILED DESCRIPTION OF PREFERRED EMBODIMENTS

Within the meaning of the invention, aryl radicals may be unsubstituted or substituted phenyl radicals. Preferred are phenyl radicals, unsubstituted or monosubstituted by halogen or alkoxy radicals. Halogen atoms may be fluorine, chlorine, or bromine atoms.

"Alk" used above and hereinafter means a straight or branched hydrocarbon radical having one to six carbons.

The compounds of Formula I are useful both in the free base form and in the form of acid addition salts. Both forms are within the scope of the invention. In practice, use of the salt form amounts to use of the base form. Appropriate pharmaceutically acceptable salts within the scope of the invention are those derived from mineral acids such as hydrochloric acid and sulfuric acid; and organic acids such as ethanesulfonic acid, benzenesulfonic acid, p-toluenesulfonic acid, and the like, giving the hydrochloride, sulfamate, ethanesulfonate, benzenesulfonate, p-toluenesulfonate, and the like, respectively.

The compounds of Formula I contain an asymmetric atom, the sulfur atom at position five, and thus are capable of existing in their individual enantiomeric forms or as a racemic mixture. The present invention is intended to include the respective optical isomers as well as the racemic modifications. Resolution of the racemic forms into the individual enantiomers may be carried out by known methods in the art. The individual enantiomers may also be prepared from optically-active precursors such as compounds of general formula II the stereoisomers of which are in turn obtained from the racemic forms by known methods of optical resolution. Neutralization of the free base of the respective diastereomers affords the individual optical isomers.

1,2,4-Benzothiadiazine derivatives of the general Formula I, in which R$^1$ represents a phenyl, methoxyphenyl, fluorophenyl, or chlorophenyl radical, R$^2$ and R$^5$, which may be the same or different, represent hydrogen, fluoro, chloro, bromo, or nitro radicals and R$^3$ represents a hydrogen atom, hydroxy, methyl, ethyl, ethoxyethyl, methoxymethyl, trifluoromethyl, hydroxymethyl, ethoxycarbonyl, dimethylaminomethyl, phenyl, fluorophenyl, or chlorophenyl radical are preferred.

The substitutents R$^2$ and R$^5$ are preferably in position seven or eight of the triazolo-1,2,4-benzothiadiazine system.

A further subject of the invention is a process for the preparation of compounds of the general Formula I in which a compound of general Formula II

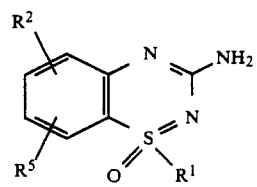

in which R$^1$, R$^2$, and R$^5$ have the above meaning, is reacted in a known manner with an ortho-ester of general Formula III $$R^3C(OR^4)_3 \qquad (III)$$

in which R$^3$ has the above meaning and R$^4$ represents a lower alkyl radical, to form a compound of general Formula IV

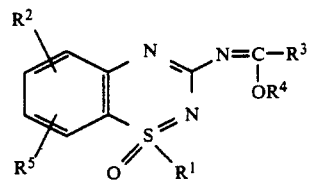

in which R$^1$, R$^2$, R$^3$, R$^4$, and R$^5$ have the above meaning, which is, without isolation, converted with ammonia to a compound of general Formula V

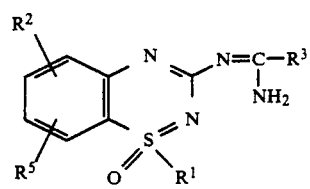

in which R$^1$, R$^2$, R$^3$, and R$^5$ have the above meaning and this compound is oxidatively cyclized in a known manner.

The compounds of general Formula II used as starting materials are known (Chem. Ber. 109, 2097, 1976) or can be prepared in analogy with the methods described therein.

The preparation of compounds of general Formula I is carried out in analogy with Federal Republic of Germany Patent Application Nos. 20 55 889 and 20 65 714.

A 3-amino-1,2,4-benzothiadiazine derivative of general Formula II is first reacted with an orthoester of general Formula III. This reaction is conveniently carried out without a solvent in an up to ten-fold excess of ortho-ester at a temperature of 120° to 160° C. The use of an acid catalyst, such as acetic acid or hydrochloric acid, has a favorable effect on the reaction. The catalyst can also be used in the form of an acid addition salt of the starting compound. The reaction time is 0.5 to two hours. After the reaction the ortho-ester is removed in a vacuum effected by a water-jet pump. The 3-imidoester residue is then converted into a 3-amidino residue. This transformation is conveniently carried out with a solution of ammonia in a lower alcohol at room temperature. Ethanol is preferably used as solvent. The reaction time is usually 2 to 20 hours. Starting material precipitated during the reaction is filtered off and after evaporation of the filtrate to dryness the residue is dissolved in a suitable solvent and submitted to oxidative cyclization. The preferred solvent is toluene and the preferred oxidizing agent lead tetraacetate. Addition of acetic acid to the reaction mixture also has favorable effects. The cyclization reaction is conveniently carried out at room temperature. The 2-alkyl-triazolo-1,2,4-benzothiadiazines obtained in accordance with the method are separated by column chromatography and/or purified by crystallization.

Another preferred method of the preparation of compounds of general Formula I is characterized in that again a compound of general Formula II is reacted in known manner with mesitylene sulfonylhydroxylamine (MSH) to form a compound of general Formula VI

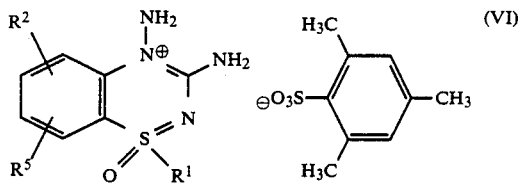

in which $R^1$, $R^2$, and $R^5$ have the above meaning, and the so formed 1-aryl-3,4-diamino-1,2,4-benzothiadiazinium-1-oxide mesitylene sulfonate (VI) either directly or after preparation of the base VII

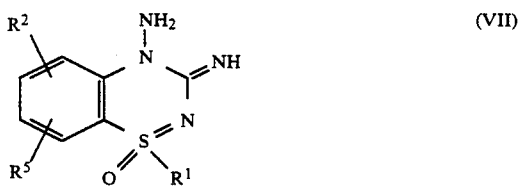

in which $R^1$, $R^2$, and $R^5$ have the above meaning, and, if desired, with an appropriate base being present, is reacted either with an appropriate carboxylic acid derivative of the general Formula VIII $R^3$-COX         (VIII)

in which $R^3$ has the above meaning and X represents a hydroxy group, a halogen atom or an alkoxy radical, or is reacted with an ortho-ester of the general Formula III to a compound of the general Formula I, in which $R^3$ may be reduced by metal hydrides, for example, lithium aluminium hydride, if desired.

This method is conducted in analogy to J. Het. Chem. 21, 1571, 1984, by reacting a compound of the general Formula II in an organic solvent, preferred dichloromethane, at 0° C. with mesitylene sulfonylhydroxylamine. The precipitated and dried compound of the general Formula VI is either transformed to the base VII or used directly for further reactions. The base VII is prepared by suspending the mesitylene sulfonate VI in an appropriate organic solvent, preferred dioxane, and reacting it with aqueous alkaline hydroxide. After separation of the precipitate the base is precipitated by diluting with iced water and recrystallized from an appropriate organic solvent, preferred ethanol. The mesitylene sulfonate VI or the base VII are boiled under reflux with an excess of a compound of the general Formulas III or VIII and, if necessary, in a polar organic solvent, preferred pyridine or tetrahydrofuran, and/or with a strong base being present, preferred sodium hydride. The compounds of the general Formula I obtained according to this method are purified by column chromatography and/or recrystallization after distillation of the solvent. If desired, the product may be reduced at position $R^3$ by a metal hydride, preferred lithium aluminium hydride, in an inert solvent, preferred tetrahydrofuran.

The compounds listed in the examples may be produced by both methods, but higher yields are obtained on the preferred second process.

The compounds of general Formula I prepared in accordance with the method possess valuable pharmacological properties, in particular they are distinguished by remarkable anxiolytic actions on the central nervous system.

A further subject of the invention is therefore the use of compounds of general Formula I in combating states of anxiety.

The compounds of general Formula I according to the invention may be applied in liquid or solid form orally or parenterally. The solvent above all used for injections is water, which in the injectable solutions contains normal additives, such as stabilizers, solubilizers, or buffers.

Such additives are e.g., tartrate and citrate buffer, ethanol, complexing agents (such as ethylenediamine tetraacetic acid and its nontoxic salts) and high-molecular polymers (such as liquid polyethylene oxide) to control viscosity. Solid carriers are e.g., starch, lactose, mannitol, methylcellulose, talc, highly-dispersed silicic acids, higher fatty acids (such as stearic acid), gelatins, agar-agar, calcium phosphate, magnesium stearate, animal and vegetable fats, solid highmolecular polymers (such as polyethylene glycol); preparations intended for oral application may contain added flavoring and/or sweetening agents if desired.

Enterally administered individual doses are in the range approximately 5 to 250 mg, preferably 10 to 100 mg. Parenteral applications are about 1 to 20 mg.

The following examples are intended as further illustrations of the invention.

EXAMPLE 1

(±)-7-Chloro-2-methyl-5-phenyl-[1,2,4]triazolo[5,1-c][1,2,4]benzothiadizine-5-oxide a.)

A 14.9 g (0.04 mol) of 3-amino-7-chloro-1-phenyl-1,2,4-benzothiadiazine-1-oxide hydrobromide and 65 g triethyl orthoacetate are boiled under reflux for two hours. A suspension is formed and after cooling the triethyl orthoacetate is distilled off in vacuo and the residue is stirred overnight with an approximately 15% ethanolic solution of ammonia (200 ml) at room temperature. The alcohol is removed in vacuo and the residue is treated with 1 liter of toluene and 20 ml of glacial acetic acid. A 25.0 g of lead tetraacetate are added in portions with vigorous stirring and stirring is continued for a further 45 minutes at room temperature. Five hundred ml of water are added, the toluene phase is separated and washed with an aqueous solution of sodium bicarbonate. After concentration the residue is chromatographed on silica gel. Eluant: methylene chloride/methanol, 20:1. 5.1 g of (±)-7-Chloro-2-methyl-5-phenyl-[1,2,4]triazolo[5,1-c][1,2,4]benzothiadiazine-5-oxide oxide are obtained in the form of colorless crystals of m. pt. 207° C. after crystallization from isopropanol. The following compounds are obtained analogously:

(±)-2-Methyl-5-phenyl-[1,2,4]triazolo[5,1-c][1,2,4]benzothiadiazine-5-oxide b.) m. pt. 212° C., crystallized from toluene.
(±)-7-Chloro-5-(3-chlorophenyl)-2-methyl-[1,2,4]triazolo[5,1-c][1,2,4]benzothiadiazine-5-oxide c.) m. pt. 195°–198° C., crystallized from ethanol.
(±)-7-Chloro-5-(4-chlorophenyl)-2-methyl-[1,2,4]triazolo[5,1-c][1,2,4]benzothiadiazine-5-oxide d.) m. pt. 249°–251° C., crystallized from ethanol.

EXAMPLE 2

(±)-8-Chloro-2-ethyl-5-phenyl[1,2,4]triazolo[5,1-c][1,2,4]benzothiadiazine-5-oxide a.)

A 2.9 g (9.9 mmol) of 3-amino-6-chloro-1-phenyl-1,2,4-benzothiadiazine-1-oxide, 15.0 g of triethyl orthopropionate and 0.6 g of glacial acetic acid are heated for one hour under reflux. The mixture is cooled, excess ortho-ester is distilled off under vacuum and the residue is treated with 50 ml of an approximately 15% solution of ammonia in ethanol. The mixture is stirred for five hours at room temperature, the precipitate formed is filtered off and the filtrate is evaporated to dryness in vacuo. The residue is dissolved in 100 ml of toluene and 4.0 g of lead tetraacetate are added in portions at room temperature.

Stirring is continued for 20 minutes at room temperature, the toluene is removed on a rotary evaporator and the residue is partitioned between water and chloroform. The organic phase is removed, washed with water and evaporated to dryness in vacuo. The residue is chromatographed on silica gel first with chloroform/methanol as eluant, then again on silica gel with toluene/ethanol, 10:1, as eluant.

The main fraction crystallizes after rubbing with ether. Colorless (±)-8-chloro-2-ethyl-5-phenyl[1,2,4]triazolo[5,1-c][1,2,4]benzothiadiazine-5-oxide, m. pt. 150° C. is obtained.

The following are obtained analogously:
(±)-8-Chloro-2-methyl-5-phenyl-[1,2,4]triazolo[5,1-c][1,2,4]benzothiadiazine-5-oxide b.) m. pt. 200° C.
(±)-7-Chloro-2-methyl-5-(2-chlorophenyl)[1,2,4]-triazolo[5,1-c][1,2,4]benzothiadiazine-5-oxide c.) m. pt. 196° C. This compound was crystallized from isopropanol and contains 0.25 mol of isopropanol.

(±)-7-Chloro-2-ethyl-5-phenyl-[1,2,4]triazolo[5,1-c][1,2,4]benzothiadiazine-5-oxide d.) m. pt. 153° C., crystallized from isopropanol.

EXAMPLE 3

(±)-7-Chloro-5-phenyl-2-trifluoromethyl-[1,2,4]triazolo[5,1-c][1,2,4]-benzothiadiazine-5-oxide a.)

To a suspension of 18.2 g of 3-amino-7-chloro-1-phenyl-1,2,4-benzothiadiazine-1-oxide in 75 ml dichloromethane is added slowly a solution of 16.1 g mesitylene sulfonylhydroxylamine (MSH) in 90 ml dichloromethane at 0° C. under stirring. Thereafter stirring is continued for one hour at room temperature and the precipitate then sucked off, washed with diethylether and air-dried. Colorless 3,4-diamino-7-chloro-1-phenyl-1,2,4-benzothiadiazine-1-oxide mesitylene sulfonate, m. pt. 225° C., are obtained. To 10.0 g thereof, suspended in 30 ml pyridine are added under stirring 8.3 g trifluoroacetic acid anhydride. After four hours of boiling the solvent is distilled in a water-jet pump vacuum. The residue is partitioned in dichloromethane/aqueous sodium bicarbonate. The organic layer is concentrated and the residue recrystallized from ethanol. A 3.9 g colorless solid product is obtained, m. pt. 167° C.

Analogously the following compounds are obtained:
(±)-7-Bromo-8-chloro-2-methyl-5-phenyl-[1,2,4]triazolo[5,1-c][1,2,4]-benzothiadiazine-5-oxide b.) m. pt. 248° C., crystallized from toluene.
(±)-7-Fluoro-2-methyl-5-phenyl-[1,2,4]triazolo[5,1-c][1,2,4]-benzothiadiazine-5-oxide c.) m. pt. 205° C., crystallized from ethanol.
(±)-7-Chloro-5-(2-fluorophenyl)-2-methyl-[1,2,4]triazolo[5,1-c][1,2,4]benzothiadiazine-5-oxide d.) m. pt. 230° C., beige crystals from ethanol.
(±)-2-Methyl-7-nitro-5-phenyl-[1,2,4]triazolo[5,1-c][1,2,4]benzothiadiazine-5-oxide e.) m. pt. 255°–258° C., yellow crystals from acetone.
(±)-7-Chloro-5-(2-methoxyphenyl)-2-methyl-[1,2,4]triazolo[5,1-c][1,2,4]benzothiadiazine-5-oxide f.) m. pt. 222°–225° C., crystallized from acetic acid ester.

EXAMPLE 4

(±)-7-Chloro-5-phenyl-[1,2,4]triazolo[5,1-c][1,2,4]benzothiadiazine-5-oxide a.)

A mixture of 7.2 g of 3,4-diamino-7-chloro-1-phenyl-1,2,4-benzothiadiazine-1-oxide mesitylene sulfonate, 9.4 ml pyridine and 12.5 ml formic acid is heated under reflux for five hours. The dark reaction mixture is concentrated by water-jet pump vacuum and the residue partitioned in dichloromethane/water. The organic phase is separated, dried and the residue is then recrystallized from isopropanol/diisopropyl ether. 1.8 g colorless crystals are obtained, m. pt. 193° C.

The following are obtained analogously:
(±)-7-Bromo-8-chloro-5-phenyl-[1,2,4]triazolo[5,1-c][1,2,4]benzothiadiazine-5-oxide b.) m. pt 264° C., crystallized from ethanol.

EXAMPLE 5

(±)-7-Chloro-2,5-diphenyl-[1,2,4]triazolo[5,1-c][1,2,4]benzothiadiazine-5-oxide a.)

A mixture of 10,1 g of 3,4-diamino-7-chloro-1-phenyl-1,2,4-benzothiadiazine-1-oxide mesitylene sulfonate in 20 ml benzoylchloride is heated under reflux for one hour. The excess of acid chloride is evaporated with a water-jet pump. The residue is triturated with a small amount of ethanol and the precipitate sucked off. After crystallization from toluene 3.6 g colorless crystals are obtained, m. pt. 271° C.

Analogously is obtained:

(±)-7-Chloro-2-(4-chlorophenyl)-5-phenyl-[1,2,4]triazolo [5,1-c][1,2,4]benzothiadiazine-5-oxide b.) m. pt. 261°–262° C., crystallized from acetonitrile.

EXAMPLE 6

(±)-7-Chloro-2-ethoxycarbonyl-5-phenyl-[1,2,4]triazolo [5,1-c][1,2,4]benzothiadiazine-5-oxide a.)

To 18.2 g of 3-amino-7-chloro-1-phenyl-1,2,4-benzothiadiazine-1-oxide is slowly added with stirring a solution of 16.1 g of mesitylene sulfonylhydroxylamine in 90 ml dichloromethane at 0° C. Stirring is continued for one hour at room temperature. Thereafter the precipitate is sucked off and washed with diethylether carefully. To the dry precipitate (30.4 g), suspended in 200 ml dioxane, 60 ml of 20% aqueous sodium hydroxide is added with stirring at 0° C. Stirring is continued for three hours at room temperature. Thereafter the precipitate is sucked off and the filtrate is poured into ice water. The precipitate is sucked off and crystallized from ethanol. A 16.0 g of colorless 4-amino-7-chloro-3,4-dihydro-3-imino-1-phenyl-1,2,4-benzothiadiazine-1-oxide, m. pt. 168° C., are obtained. A 6.5 g thereof in 25 ml ethyl oxalate chloride is heated for five hours to 80° C. The excess of acid chloride is distilled and the residue partitioned in dichloromethane/aqueous sodium hydrogencarbonate. The organic solvent is distilled in vacuo and the residue crystallized from ethanol, recrystallized from toluene and again from ethanol. A 3.5 g colorless crystals are obtained, m. pt. 239° C.

Analogously are obtained:

(±)-7-Chloro-2-methoxymethyl-5-phenyl-[1,2,4]triazolo-[5,1-c][1,2,4]benzothiadiazine-5-oxide b.) m. pt. 222°–225° C. from acetic acid ester.

(±)-7-Chloro-2-hydroxymethyl-5-phenyl-[1,2,4]triazolo-[5,1-c][1,2,4]benzothiadiazine-5-oxide c.) m. pt. 222°–225° C. from acetic acid ester, is obtained by reduction of 6a.) with lithium aluminium hydride.

EXAMPLE 7

(±)-7-Chloro-2-dimethylaminomethyl-5-phenyl 1,2,4]triazolo[5,1-c][1,2,4]benzothiadiazine-5-oxide To a mixture of 4.5 g of 4-amino-7-chloro-3,4-dihydro-3-imino-1-phenyl-1,2,4-benzothiadiazinium-1-oxide, prepared according to Example 6, and 3.9 g of trimethyl dimethylaminoorthoacetate, 3 ml of acetic acid is added. The mixture is then heated up to 80° C. for five hours and after this distilled in vacuo effected by water-jet pump. The residue is triturated with acetic acid ester. The precipitate is sucked off and twice purified by silica gel column chromatography with dichloromethane/methanol 100:5 as eluant. The main fraction is concentrated and recrystallized from ethyl acetate. 2.3 g colorless crystals are obtained, m. pt. 202° C.

EXAMPLE 8

(±)-7-Chloro-2-hydroxy-5-phenyl-[1,2,4]triazolo[5,1-c][1,2,4]benzothiadiazine-5-oxide To a solution of 7.0 g of 4-amino-7-chloro-3,4-dihydro-3-imino-1-phenyl-1,2,4-benzothiadiazine-1-oxide, prepared according to Example 6, in 250 ml tetrahydrofurane are added 0.68 g of sodium hydride (80%) in portions. After stirring for 30 minutes at room temperature 2.4 ml ethyl chloroformate, dissolved in 10 ml tetrahydrofuran, are added dropwise. The mixture is stirred at room temperature for three hours, then separated from the precipitated sodium chloride and concentrated. The residue is dissolved in 150 ml toluene and boiled for 16 hours under reflux. The precipitated product is sucked off and crystallized from dimethylformamide/methanol as colorless crystals, m. pt. 343°–348° C.

In order to evaluate the pharmacological action of the compounds of general Formula I the following comparison experiments were carried out:

COMPARATIVE TESTS

Methods

1. Experimental Animals

Experimental animals used were male mice (NMRI, origin: Ivanovas, Kissleg) of weight 18 to 25 g. The animals were allowed food and water ad lib., but, according to the test, they were fasted for two to 16 hours before the beginning of the test with water allowed ad lib.

2. Substances

The substances under test were applied orally by means of a stomach tube in a 0.8% methocel suspension 30 minutes before the start of the test.

3. Test Procedures 3.1. Anxiolytic Activity

The model for testing for anxiolytic activity is based on the experimental creation of a conflict in the animals by counteracting the natural exploratory tendencies of the animals with an anxiety-inducing stimulus (aversive foot shock, aversive illumination).

a. Punished Exploratory Behavior (4 plate test):

The test box has a metal base consisting of four rectangles of equal size. After placing the animal in the box it can freely explore for 15 seconds. Then every transition from one metal plate of the base to another is punished by a mild foot shock (1.5 mA for 0.5 seconds). The number of tolerated foot shocks within one minute is the measure of the anxiolytic activity of the substance. The average number of accepted foot shock by the control animals was taken as 100%. Ten animals were examined per dose.

b. Unpunished Exploratory Behavior (lightdark preference):

The testing equipment consists of a larger, brightly illuminated compartment and a smaller dark compartment. The animal is placed in the dark compartment and observed for ten minutes. The number of transitions between the compartments and the time spent in the two compartments are measured. The average number of transitions between the compartments of the control animals is taken as 100%. Ten animals were tested per dose.

3.2 Motility Test

The spontaneous motility was measured simultaneously for a test group of five animals each for 30 minutes in two opaque cages (length 50 cm, width 25 cm, height 30 cm) using three infrared light barriers in each case. The sum of the impulses registered for the control group during this period was taken as 100% and the deviation in the case of the test group from this value was calculated in percent.

3.3. Test for Effect on Duration of Anesthesia

Seventy mg/kg (10 ml/kg body weight) of hexobarbital sodium were injected into a tail vein within a period of 15 seconds. Ten animals were used per dose. The criterion for the end of anesthesia was the moment when the animal roused itself from lying on its side. The average duration of anesthesia in the control animals was taken as 100 and the increases measured were calculated as a percentage of this value.

The results of the tests are shown in Table 1 below.

TABLE 1

| | Pharmacological and Biochemical Activities | | | | | |
|---|---|---|---|---|---|---|
| | Example Numbers | | | | | |
| Model | 1a | 1c | 2c | 4a | 4b | Diazepam |
| Anxiolytic Activity (punished exploration) | 7.5–45 mg/kg 30% to 172% increase | 15 mg/kg 35% increase | 30 mg/kg 66% increase | 15 mg/kg 45% increase | 12.5 mg/kg 34% increase | 1–4 mg/kg 32% bis 179% increase |
| Anxiolytic Activity (unpunished exploration) | 20–30 mg/kg 24% to 40% increase | | | | | 2 mg/kg 43% increase 5 mg/kg 33% decrease |
| Spontaneous Motility | 50 mg/kg 45% increase | 15 mg/kg 12% increase | 30 mg/kg 6% increase | 100 mg/kg no effect | 12.5 mg/kg 83% increase | 5 mg/kg 67% decrease |
| Ataxia Threshold | >100 mg/kg | >100 mg/kg | >100 mg/kg | >100 mg/kg | >400 mg/kg | 5 mg/kg |
| Hypnotic Activity (increase in sleep time) | 25 mg/kg 123% increase 50 mg/kg 175% increase | 15 mg/kg 6% increase | 30 mg/kg 96% increase | 100 mg/kg 224% increase | 25 mg/kg 21% increase | 2 mg/kg 286% increase 4 mg/kg 320% increase |
| Receptor binding: benzodiazepine rec. GABA-Ratio | $K_d = 1.5\ \mu M$ R = 1.6 part. agonist | $K_d = 10\ \mu M$ | $K_d = 20$ nM R = 1.1 part. ago. | $K_d = 3.5\ \mu M$ R = 1.4 part. ago. | $K_d = 100\ \mu M$ | $K_d = 64$ nM R = 2.9 agonist |
| $LD_{50}$ | 1600 mg/kg | >400 mg/kg | >400 mg/kg | >400 mg/kg | >400 mg/kg | 700 mg/kg |

">": no effect up to this highest examined dosage

The compounds of general Formula I show anxiolytic activity in punished exploration conflict (four plate test, C. Aron, et al, Neuropharmacology, 10, 459–469, 1970) and in unpunished exploration conflict (light-dark preference test). Thus, Example 1a at 7.5 to 45 mg/kg displays an activity which is comparable with that of diazepam (1 to 4 mg/kg). However, whilst diazepam lowers spontaneous motility by 67% even at 5 mg/kg, Example 1a effects an increase in motility around 45% at 50 mg/kg. Moreover, the threshold for ataxia in the case of diazepam is approximately 5 mg/kg, whilst Compound 1a has no atactic effect up to 100 mg/kg.

We claim:

1. A compound of the formula

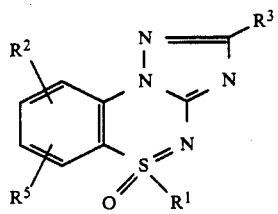

in which
R$^1$ represents phenyl, unsubstituted or monosubstituted by halogen or alkoxy having one to six carbon atoms;
R$^2$ and R$^5$ which may be the same or different, represent hydrogen, halogen, or a nitro group; and
R$^3$ represents a hydrogen or hydroxy radical, an alkyl, alkoxyalkyl or alkoxy carbonyl radical with up to four carbon atoms, unsubstituted or substituted by halogen, hydroxy, amino, alkyl amino or dialkyl amino radicals or a phenyl radical, unsubstituted or substituted by halogen; or a pharmaceutically acceptable acid addition salt thereof, or its optical isomer thereof.

2. A compound according to claim 1, in which
R$^1$ represents a phenyl, methoxyphenyl, fluorophenyl, or chlorophenyl radical;
R$^2$ and R$^5$ represent hydrogen, chloro, fluoro, or a nitro radical; and
R$^3$ represents a hydrogen atom or hydroxy, methyl, ethyl, methoxymethyl, trifluoromethyl, ethoxyethyl, hydroxymethyl, ethoxycarbonyl, dimethylaminomethyl, phenyl, fluorophenyl, or chlorophenyl radical.

3. A compound according to claim 2 in which the R$^2$ and R$^5$ substituent is in position seven or eight of the triazolo-1,2,4-benzothiadiazine system.

4. A compound according claim 3, and being 7-chloro-2-methyl-5-phenyl-[1,2,4]triazolo[5,1-c][1,2,4]benzothiadizine-5-oxide.

5. A compound according to claim 3, and being 7-chloro-5-(3-chlorophenyl)-2-methyl-[1,2,4]triazolo[5,1-c][1,2,4]benzothiadiazine-5-oxide.

6. A compound according to claim 3, and being 7-chloro-2-methyl-5-(2-chlorophenyl)[1,2,4]triazolo[5,1-c][1,2,4]benzothiadiazine-5-oxide.

7. A compound according to claim 3, and being 7-chloro-5-phenyl-[1,2,4]triazolo[5,1-c][1,2,4]benzothiadiazine-5-oxide.

8. A compound according to claim 3, and being 7-bromo-8-chloro-5-phenyl-[1,2,4]triazolo-[5,1-c][1,2,4]benzothiadiazine-5-oxide.

9. A pharmaceutical composition comprising an antianxiolytically effective amount of a compound according to claim 1 in admixture with a common pharmaceutical additive, diluent or carrier.

10. A method for treating anxiety which comprises administering to a host suffering therefrom a pharmaceutical composition according to claim 9 in unit dosage form.

* * * * *